US010188320B2

(12) United States Patent
Radl et al.

(10) Patent No.: US 10,188,320 B2
(45) Date of Patent: Jan. 29, 2019

(54) LAPAROSCOPIC TISSUE THICKNESS MEASURING DEVICE AND METHOD OF USE

(71) Applicant: Boehringer Technologies, LP, Phoenixville, PA (US)

(72) Inventors: Christopher L. Radl, Malvern, PA (US); Steven C. Moulden, West Chester, PA (US)

(73) Assignee: Boehringer Technologies, LP, Phoenixville, PA (US)

( * ) Notice: Subject to any disclaimer, the term of this patent is extended or adjusted under 35 U.S.C. 154(b) by 288 days.

(21) Appl. No.: 15/203,331

(22) Filed: Jul. 6, 2016

(65) Prior Publication Data

US 2017/0065209 A1    Mar. 9, 2017

Related U.S. Application Data

(60) Provisional application No. 62/215,269, filed on Sep. 8, 2015.

(51) Int. Cl.
*A61B 5/00* (2006.01)
*A61B 5/107* (2006.01)
(Continued)

(52) U.S. Cl.
CPC ............ *A61B 5/1076* (2013.01); *A61B 90/06* (2016.02); *A61B 17/00234* (2013.01);
(Continued)

(58) Field of Classification Search
CPC ... A61B 90/06; A61B 2090/061; A61B 5/107; A61B 5/1072; A61B 5/1076
See application file for complete search history.

(56) References Cited

U.S. PATENT DOCUMENTS

| 4,527,724 A | 7/1985 | Chow et al. |
| 4,726,121 A * | 2/1988 | Ray ........................ G01B 3/20 33/512 |

(Continued)

FOREIGN PATENT DOCUMENTS

EP    1974676 B1    10/2010

OTHER PUBLICATIONS

International Search Report for PCT/US2016/049231 dated Nov. 16, 2016.

*Primary Examiner* — Max Hindenburg
(74) *Attorney, Agent, or Firm* — Caesar Rivise, PC

(57) ABSTRACT

A laparoscopic device and method of use for measuring the thickness of tissue is disclosed. The instrument includes an elongated tubular housing, an elongated shaft, a pair of jaws, an actuating mechanism and a tissue thickness indicator. The tissue thickness indicator includes an indicator scale on the housing and a marker located on a proximal portion of the shaft. The shaft is displaceable within the housing against the bias of a spring and is coupled to the jaws to open the jaws when the shaft is moved distally by the actuating mechanism, whereupon the tissue can be located between the open jaws. The actuator mechanism can then be released, whereupon the jaws close on the interposed tissue and move the shaft in the proximal direction so that marker is disposed adjacent to the indicator scale to thereby provide a readily visible indication of the thickness of the tissue.

20 Claims, 2 Drawing Sheets

(51) Int. Cl.
*A61B 90/00* (2016.01)
*A61B 17/00* (2006.01)
*A61B 17/29* (2006.01)
*A61B 17/068* (2006.01)

(52) U.S. Cl.
CPC ... *A61B 17/068* (2013.01); *A61B 2017/00862* (2013.01); *A61B 2017/2923* (2013.01); *A61B 2017/2932* (2013.01); *A61B 2090/061* (2016.02)

(56) References Cited

U.S. PATENT DOCUMENTS

| | | | |
|---|---|---|---|
| 5,327,908 A | | 7/1994 | Gerry |
| 5,533,521 A | | 7/1996 | Granger |
| 6,957,498 B2 | * | 10/2005 | Tsai ........................ G01B 3/205 33/610 |
| 8,276,288 B1 | * | 10/2012 | Yu ......................... A61B 5/1072 33/464 |
| 8,826,557 B2 | * | 9/2014 | Yang ........................ G01B 3/20 33/609 |
| 8,893,946 B2 | | 11/2014 | Boudreaux et al. |
| 9,427,318 B2 | * | 8/2016 | Hjelle .................... A61B 5/107 |
| 2009/0012556 A1 | | 1/2009 | Boudreaux et al. |

* cited by examiner

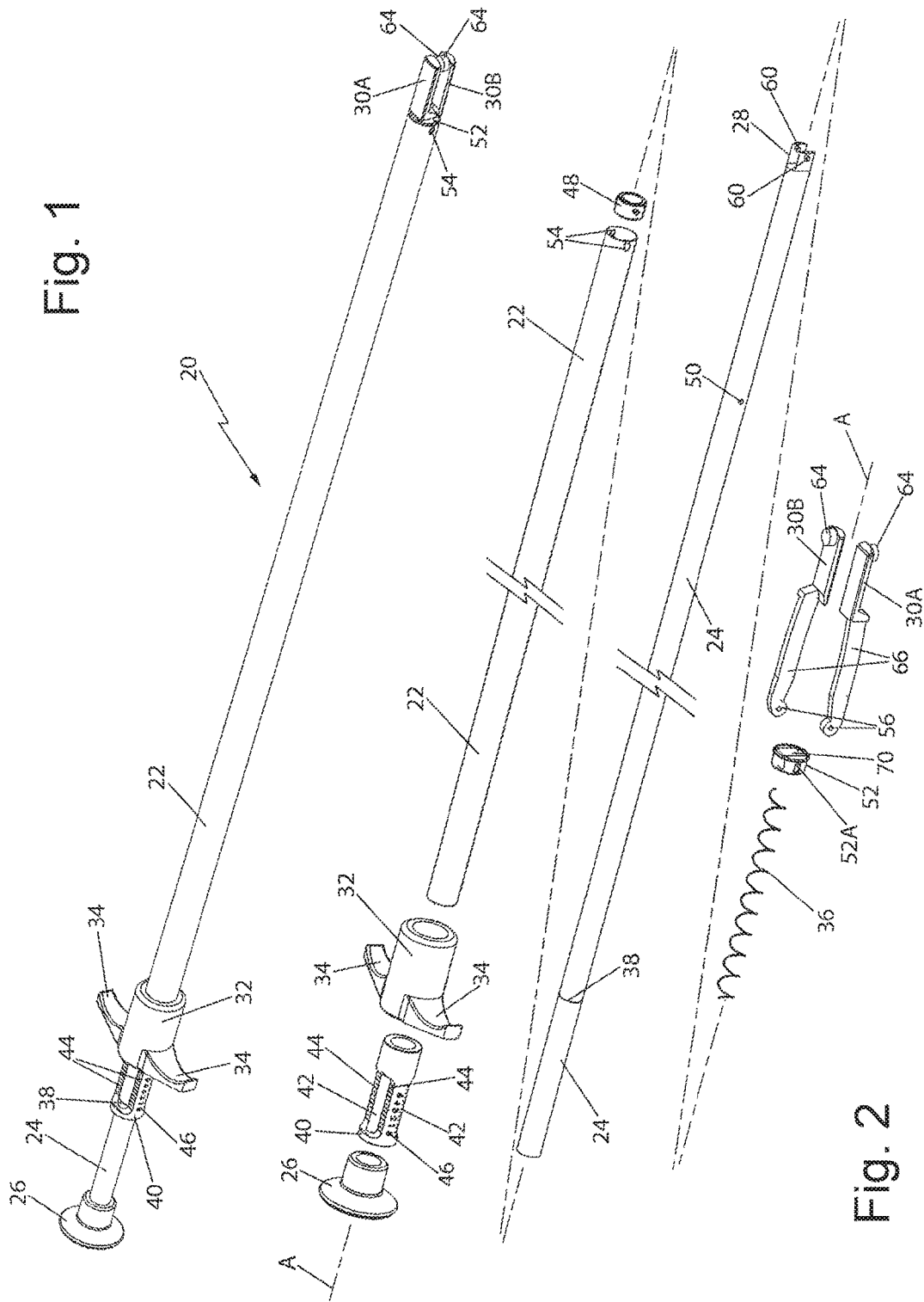

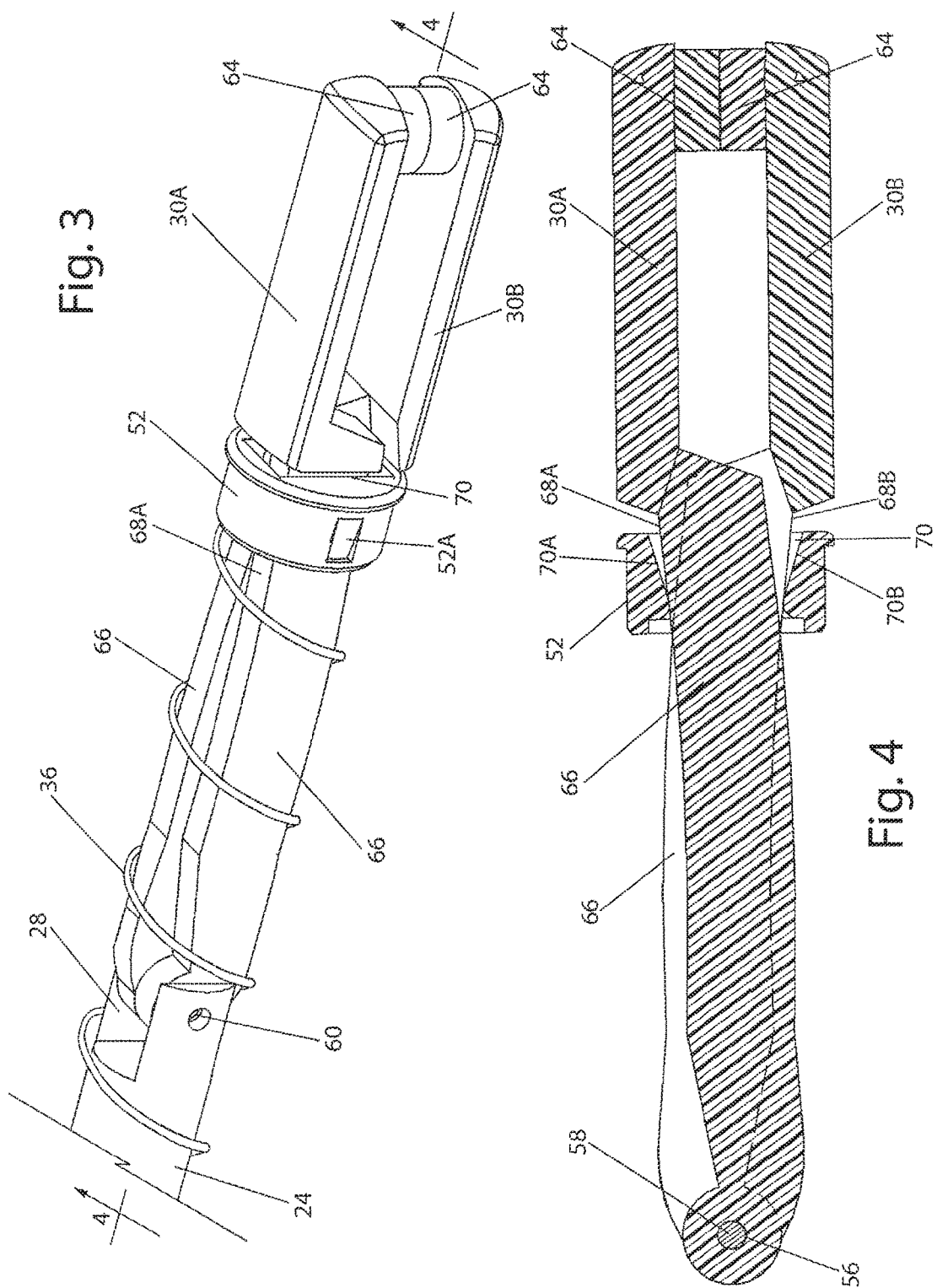

LAPAROSCOPIC TISSUE THICKNESS MEASURING DEVICE AND METHOD OF USE

CROSS-REFERENCE TO RELATED APPLICATIONS

This utility application claims the benefit under 35 U.S.C. § 119(e) of Provisional Application Ser. No. 62/215,269 filed on Sep. 8, 2015 entitled Laparoscopic Tissue Thickness Measuring Device. The entire disclosure of the provisional application is incorporated by reference herein.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISK

Not Applicable

FIELD OF THE INVENTION

The disclosed invention relates to medical devices and more particularly to laparoscopic devices for measuring the thickness of tissue and a method of using the same.

BACKGROUND OF THE INVENTION

During some laparoscopic surgical procedures, such as the sleeve gastrectomy, laparoscopic staplers are used to staple layers of tissue together. The manufacturers of the staplers provide different staple load sizes for varying tissue thicknesses. However, there are no generally acceptable instruments to measure the tissue thickness. Therefore, the surgeons currently have to rely on anatomy and or "feel" to choose the correct staple load. This creates an increased risk of bleeding and staple line leak.

The patent literature includes various devices for measuring the thickness of tissue within the body of a being. See for example, U.S. Pat. No. 5,327,908 (Gerry), U.S. Pat. No. 5,533,521 (Granger), and U.S. Pat. No. 8,893,946 (Boudreaux et al.). While such prior art devices may be generally suitable for their intended purposes, they leave much to be desired from various standpoints, such a simplicity of construction, ease of use, cost, etc. Thus a need exists for an instrument which is simple in construction, low in cost, easy to use and which will effectively measure the thickness of tissue within the body of a being. The subject invention addresses those needs.

All references cited and/or identified herein are specifically incorporated by reference herein.

SUMMARY OF THE INVENTION

In accordance with one aspect of this invention a laparoscopic device for measuring the thickness of tissue is provided. The device comprises an elongated tubular housing, a tissue thickness indicator, a reciprocating member, and a pair of jaws. The elongated tubular housing has a proximal end portion. The tissue thickness indicator is located at the proximal end portion of the tubular housing. The reciprocating member is coupled to the tissue thickness indicator and is configured for reciprocating movement within the tubular housing. Each of the jaws has a tip portion. At least one of the jaws is movable with respect to the other of the jaws to define an openable and closable mouth between the tip portions of the jaws. The mouth is configured to be opened upon movement of the reciprocating member through the tubular housing, whereupon the mouth is enabled to receive tissue therein. The reciprocating member is normally biased by a force to automatically close the mouth, whereupon the closing of the mouth moves the reciprocating member a greater distance than the distance separating the tip portions of the jaws. The movement of the reciprocating member causes the tissue thickness indicator to provide a readily visible indication of the distance separating the tip portions of the jaws, and hence the thickness of tissue within the openable mouth.

In accordance with a preferred aspect of the device of this invention the reciprocating member comprises an elongated shaft having a proximal end portion and the tissue thickness indicator comprises an indicator scale and a marker. One of the indicator scale and the marker is fixedly secured to the proximal end portion of the tubular housing. The other of the indicator scale and the marker is fixedly secured to the proximal end portion of the shaft. Closing of the mouth of the device moves the marker and the indicator scale with respect to each other a greater distance than the distance separating the tip portions of the jaws to thereby provide the readily visible indication of the thickness of tissue within the openable mouth.

In accordance with another preferred aspect of the device of this invention the force biasing the shaft is substantially constant to cause the tip portions of the jaws to apply a relatively constant force to the tissue within the mouth, and the force biasing the shaft is provided by a preloaded compression spring.

In accordance with another preferred aspect of the device of this invention both of the jaws are movable and are pivotably connected to each other.

In accordance with another preferred aspect of the device of this invention each of the jaws comprises a first cam surface and wherein the tubular housing includes a distal end portion at which second cam surfaces are located. The second cam surfaces are configured to engage the first cam surfaces to pivot the jaws with respect to each other to open the mouth upon the movement of the elongated rod within the elongated tubular housing.

In accordance with another preferred aspect of the device of this invention an actuating mechanism for moving the shaft is provided. The actuating mechanism comprises a thumb button coupled to the shaft and a finger grip member coupled to the tubular housing. The thumb button is configured to be manually moved with respect to the finger grip member to move the shaft with respect to the tubular housing to effect the opening of the openable mouth.

In accordance with another preferred aspect of the device of this invention the marker is located on the elongated rod and the elongated housing comprises a sleeve section through which the distal portion of the elongated rod extends. The sleeve section has a window and indicia extending along the window.

Another aspect of this invention is a method of measuring the thickness of tissue within the body of a patient. The method entails providing a laparoscopic device comprising an elongated tubular housing, a tissue thickness indicator, a reciprocating member and a pair of jaws. The elongated tubular housing has a proximal end portion. The tissue thickness indicator is located at the proximal end portion of the tubular housing. The reciprocating member is coupled to the tissue thickness indicator and is configured for reciprocating movement within the tubular housing. Each of the jaws has a tip portion. At least one of the jaws is movable with respect to the other of the jaws to define an openable and closable mouth between the tip portions of the jaws. The laparoscopic device is inserted into the body of the patient to a situs of the tissue. A force is applied to a portion of the device against a bias on the reciprocating member to cause the reciprocating member to move through the tubular housing to open the mouth. The device is manipulated to locate the tissue in the open mouth and the force on the portion of the device is released, whereupon the mouth automatically closes. The reciprocating member is configured whereupon the closing of the mouth moves the reciprocating member a greater distance than the distance separating the tip portions of the jaws and the movement of the reciprocating member causes the tissue thickness indicator to provide a readily visible indication of the distance separating the tip portions of the jaws, and hence the thickness of tissue within the openable mouth.

In accordance with one preferred aspect of the method of this invention the method forms a portion of a bariatric procedure on the patient.

Another aspect of this invention is a laparoscopic device for measuring the thickness of tissue. The device has a longitudinal axis and comprises a first elongated member, a second elongated member, a first jaw, a second jaw, a biasing member, and a tissue thickness indicator. The first and second elongated members extend parallel to the longitudinal axis. One of the first and second elongated members is configured for reciprocation with respect to the other of the first and second elongated members. At least one of the jaws is coupled to the other of the first and second elongated members. The first and second jaws are moveable along the axis. At least one of the first and second jaws is pivotable with respect to the other of the first and second jaws from a closed state to one of various open states, and vice versa. The distance between the jaws is different in each of the various open states. The biasing member is configured for biasing the jaws to the closed state. The tissue thickness indicator is coupled to the jaws for indicating the distance between the jaws.

In accordance with another preferred aspect of the device of this invention the first and second jaws are pivotable with respect to each other.

In accordance with another preferred aspect of the device of this invention the indicator comprises a scale with plural indicia spaced at fixed positions along the scale and a marker moveable with respect to the scale. The marker is movable from a first position at one of the indicia when the jaws are in the closed state to a second position at another of the indicia when the jaws are in one of the open states. The distance between the one of the indicia and the other of the indicia provides an indication of the distance between the jaws. Also the distance between the one of the indicia and the other of the indicia is at least equal to the distance between the jaws.

BRIEF DESCRIPTION OF THE DRAWING FIGURES

FIG. 1 is an isometric view of one exemplary embodiment of a laparoscopic device for measuring the thickness of tissue constructed in accordance with this invention;

FIG. 2 is an exploded isometric view of the laparoscopic device shown in FIG. 1;

FIG. 3 is an enlarged isometric view of the distal end of the laparoscopic device shown in FIGS. 1 and 2, but with a portion of the device removed in the interest of clarity; and FIG. 4 is a vertical sectional view of a portion of the device shown in FIG. 3 taken along line 4-4 of FIG. 3.

DETAILED DESCRIPTION OF THE PREFERRED EMBODIMENTS

Referring now to the drawings wherein like characters refer to like parts there is shown at 20 in FIG. 1 one exemplary embodiment of a laparoscopic device for measuring the thickness of tissue constructed in accordance with this invention. The device 20 is in the form of an elongated instrument configured for laparoscopic insertion into the body of a patient to the site of internal tissue whose thickness is to be measured so that it can be effectively stapled. To that end, the instrument has a longitudinal axis A and includes a distal end portion having a pair of jaws centered on that axis and forming an openable/closeable mouth into which the tissue to be measured is located. The proximal end portion of the device includes an actuating mechanism for opening and closing the device's mouth and a tissue thickness indicator mechanism which is coupled to the actuating mechanism to provide a readily visible indication of the thickness of tissue within the device's mouth.

The device 20 basically comprises linear tubular housing 22 through which an elongated linear rod or shaft 24 extends. The tubular housing can be formed of any suitable material and in the exemplary embodiment it is a 304 stainless steel seamless tube. The shaft 24 can be formed of any suitable material and in the exemplary embodiment it is formed of Nylon or Acrylonitrile butadiene styrene (ABS). The proximal end of the shaft 24 is in the form of a thumb button 26, which serves as one portion of the actuating mechanism for opening and closing the instrument's mouth. The thumb button can be formed of any suitable material and in the exemplary embodiment the thumb button is formed of ABS. The distal end of the shaft 24 is best seen in FIGS. 2 and 3 and is in the form of a yoke 28 mounting a pair of spring-biased pivotable jaws 30A and 30B. The jaws can be formed of any suitable material and in the exemplary embodiment each jaw is formed of stainless steel or Polyphenylene sulfide (PPS) plastic. The shaft 24 is configured to be reciprocated (e.g., slid) within the tubular housing upon the operation of the actuating mechanism to cause the jaws to move relative to each other.

The details of the construction and operation of the pivotable jaws 30A and 30B will be described later. Suffice it for now to state that each of the jaws includes a tip. The tips define the openable/closeable mouth therebetween. In particular, when the shaft 24 is moved (e.g., slid) distally through the housing 22 by the actuating mechanism, that action causes the jaws to pivot with respect to each other, whereupon the tips of the jaws are separated from each other. The resulting space between those tips forms the mouth of the instrument. After the instrument's mouth has been opened the instrument can be manipulated so that the tissue to be measured is located within the open mouth. Then the jaws can be closed by the actuating mechanism to move (e.g., slide) the shaft in the proximal direction to bring the tips of the jaws into engagement with the tissue interposed therebetween. In accordance with one exemplary embodiment of this invention the amount of displacement or movement of the shaft is directly proportional the amount of opening of the mouth of the instrument. The tissue thickness indicator mechanism is coupled to the jaws by the shaft 24 to thereby provide a precise, accurate and readily visible indication of the distance separating the tips of the jaws (and hence the thickness of the tissue interposed between the tips of the jaws) to the user of the instrument.

The actuating mechanism for effecting the opening and closing of the jaws comprises the heretofore identified thumb button 26 and a finger grip member 32. The finger grip member 32 is fixedly secured at the proximal end of the tubular housing 22 and is in the form of a short length tubular body having a pair of finger-like projections 34 extending diametrically outward from the body. The finger grip member can be formed of any suitable material and in the exemplary embodiment the finger grip member 32 is formed of ABS. The actuating mechanism is operated by the user of the instrument pressing on the thumb button 26 with his/her thumb while holding the finger-like projections 34 with his/her fingers, whereupon the shaft 24 is slid through the housing in the distal direction against the bias of a spring 36 (to be described later).

The tissue thickness indicator mechanism basically comprises a marker 38 (FIG. 2) located on the proximal end portion of the shaft 24 and a calibration or indicator sleeve 40 fixedly secured to the proximal end of the finger grip member 32. The indicator sleeve 40 is a tubular member having a central passageway through which the shaft 24 extends. The indicator sleeve can be formed of any suitable material and in the exemplary embodiment the indicator sleeve is formed of ABS. The marker 38 and the indicator sleeve 40 are moveable relative to each other. The indicator sleeve 40 includes a pair of diametrically opposed windows 42 through which a proximal portion of the shaft 24 can be seen. Each window 42 has a pair of indicator scales 44 extending along at least a portion of its length on either side of the window. The proximal portion of the shaft includes the marker 38 on its outer surface so that the marker can be seen in both of the windows 42 adjacent the indicator scales 44 of those windows. The marker 40 can be of any suitable form, e.g., a pointer, a line, a color bar, etc. In the exemplary embodiment shown in FIG. 2, it constitutes a line. The indicator scales 44 are in the form of indicia, e.g., marking lines equidistantly spaced apart from each other. The indicator sleeve also includes indicia 46 in the form of sequential numbers starting at "0" and disposed at equidistantly spaced locations adjacent the marking lines of the associated scale. Those lines and their associated numerical indicia represent the distance along the scale from the proximal end of the scale. Thus, when the shaft is moved or displaced to any position wherein its marker 38 is located adjacent any one of the marking lines of the scale 44 that indicates the thickness of the tissue in millimeters since the displacement of the shaft is directly proportional to the spacing between the tips of the jaws.

In accordance with one exemplary embodiment of this invention the instrument is constructed so that the change in jaw opening distance at the tips of the jaws is greater than the distance traveled by the indicator marker 38 with respect to the scale. For example, as the jaw opening distance increases from 1 mm to 5 mm, the indicator marker 38 on the shaft 24 moves a distance of 11 mm (a ratio of 1:2.75) along the scale. This makes it easier to read the scale, since a small displacement of the jaw tips with respect to each other will result in a significantly greater displacement of the shaft (and hence the marker on the shaft) with respect to the scale on the indicator sleeve.

A bushing 48 is fixedly mounted on the shaft 24 via a pin (not shown) extending through a transverse hole 50 (FIG. 2 in the shaft. The bushing can be formed of any suitable material and in the exemplary embodiment the bushing 48 is formed of stainless steel. The bushing 48 serves to keep the shaft centered within the tubular housing and serves as a stop against which the proximal end of the spring 36 bears. The spring 36 serves to normally bias the shaft 24 longitudinally within the tubular housing 22 to its most proximal longitudinally located position (hereinafter the "retracted" position). In the retracted position the tips of the jaws which are coupled to the shaft are in engagement with each other so that the mouth of the instrument closed, like shown in FIG. 1. The spring is a helical compression member which can be formed of any suitable material. In the exemplary embodiment shown the spring is formed of 302 Stainless Steel. In order to bias the rod into the retracted position the distal end of the spring bears against a nose bushing 52 located at the distal end of the tubular housing. The nose bushing can be formed of any suitable material and in the exemplary embodiment the nose bushing 52 is formed of stainless steel or PPS. The nose bushing will be described in detail shortly. Suffice it for now to state that the nose bushing includes a central passageway 70 through which portions of the jaws 30A and 30B extend and which passageway includes a pair of cam surfaces configured to be engaged by respective surfaces of the jaws to facilitate the opening and closing of those jaws. The nose bushing is fixedly secured to the distal end of the tubular housing by a pair of short ramp-like detents 54 (FIG. 2) at the distal end of the housing which snap-fit within respective, correspondingly shaped recesses 52A (FIG. 3) in the periphery of the nose bushing.

As best seen in FIG. 3 the proximal end of the spring 36 is in engagement with the inner end of the nose bushing 52 so that the spring is compressed between that bushing and the bushing 48 on the shaft 24. That action produces the bias force on the shaft tending to slide and hold it in the retracted position. In accordance with one preferred aspect of the invention the bias force produced by the spring is relatively constant to ensure that the force applied by the tips of the jaws to the tissue interposed therebetween is relatively constant. This is important because tissue is compressible. Therefore, the applied force impacts thickness measurement, thereby making a relatively constant force desirable. The relatively constant bias force provided by the jaws of the instrument 20 is achieved by taking a long, e.g., six inch, spring 36 and assembling the instrument such that the spring is compressed to 1.5 inches in length during assembly and held in its compressed state between the bushings 48 and 52 such that the force applied by the jaws is as follows. At 0 mm displacement of the shaft, i.e., when the shaft is in its retracted position, the force applied between the tips of the jaws is 169 grams. When the rod is displaced 1 mm, the force applied between the tips of the jaws is 179 grams. When the rod is displaced 5 mm, the force applied between the tips of the jaws is 218 grams. Therefore, with such an arrangement the applied force only varies by ±12 percent over the measuring range.

It should be pointed out at this juncture that spring pre-compression alone does not necessarily ensure a relatively constant force. It would be easy to configure the device such that it applies a force of 10 grams at 0 mm and a force of 218 grams at 5 mm giving a force that varies by ±90% over the measurement range. In such a case there is only a small amount of preload.

Turning now to FIGS. 3 and 4, the details of the jaws 30A and 30B will now be described. To that end, as can be seen each of the jaws includes a proximal end having a pivot hole 56 therein. The pivot holes of the two jaws are axially aligned and configured to receive a pivot or dowel pin 58.

The pivot pin can be formed of any suitable material and in the exemplary embodiment the pin is formed of 18-8 stainless steel. The pin extends through axially aligned holes 60 in the yoke 28 at the distal end of the shaft 24 and through the axially aligned holes 56 of the jaws. Thus, the jaws 30A and 30B are pivotable about the axis of the pin 58. The distal end portion of each jaw is in the form of an offset flange 62 having a free end from which a tip 64 projects. The tips 64 form the mouth of the instrument 20. The intermediate portion of each of the jaws, i.e., the portion of each of the jaws between its offset flange 62 and its pivot hole 56, is in the form of an elongated leg having an inclined outer cam surface. In particular, the jaw 30A includes an inclined cam surface 68A and the jaw 30B includes an inclined cam surface 68B. Those cam surfaces are arranged to engage and ride along respective cam surfaces of the passageway 70 in the nose bushing 52 to pivot the jaws about the pivot pin 60 as the shaft is slid in the distal direction to thereby open the jaws. In particular, the nose bushing 52 includes the heretofore identified passageway 70. That passageway is centrally located in the bushing and has a pair of cam surfaces 70A and 70B on opposite sides of the passageway. The cam surface 70A is configured to be engaged by the cam surface 68A of the jaw 30A, while the cam surface 70B is configured to be engaged by the cam surface 68B of the jaw 30B.

During use of the instrument 20, e.g., for a bariatric procedure, the operator or user places the instrument's distal end into the peritoneal space via a cannula. Depressing the thumb button 26, while holding the finger grip 32, moves the shaft 24 in the distal direction to force the jaws distally outward from the nose bushing 52 against the bias of the spring 36. That action causes the inclined cam surfaces 68A and 68B to ride along the cam surfaces 70A and 70B of the nose bushing, whereupon the jaws pivot in opposite rotational directions about the axis of the pivot pin 60, thereby opening the mouth of the jaws. When the shaft is displaced to its maximum extended (distal) position, the tips of the jaws will be at their maximum spacing from each other. With the jaws open, the instrument can be manipulated so that the tissue to be measured is located within the open mouth. At that time, the operator releases the pressure on the thumb button 26, whereupon the bias force provided by the compressed spring 36 will carry the shaft 24 back toward its retracted position until the tips 64 of the jaws 30A and 30B engage the tissue between them. When that has occurred the shaft 24 will have moved to a position wherein its marker 38 will be aligned with the indicia on the scale 44 indicating the spacing between the tips of the jaws and hence the thickness of the interposed tissue.

It should be pointed out at this juncture that the device 20 as described above is merely exemplary of various components and arrangements that can be used to achieve the ends of this invention. Thus other devices can be constructed in accordance with the teaching of this invention.

Without further elaboration the foregoing will so fully illustrate our invention that others may, by applying current or future knowledge, adopt the same for use under various conditions of service.

We claim:

1. A laparoscopic device for measuring the thickness of tissue, said device comprising:
    an elongated tubular housing having a central longitudinal axis and a proximal end portion;
    a tissue thickness indicator comprising a tubular section, an indicator scale and a marker, said tubular section being located at said proximal end portion of said elongated tubular housing and coaxial with said central longitudinal axis, said indicator scale comprising indicia disposed linearly along said central longitudinal axis;
    a reciprocating linear member coupled to said tissue thickness indicator, said reciprocating linear member having a first portion configured for reciprocating linear movement within said tubular housing along said central longitudinal axis and a second portion configured for reciprocating linear movement along said central longitudinal axis in said tubular section, wherein one of said indicator scale and said marker is fixedly located at said proximal end portion of said elongated tubular housing and the other of said indicator scale and said marker is fixedly located at said proximal end portion of said reciprocating linear member; and
    a pair of jaws, each of said jaws having a tip portion, at least one of said jaws being movable with respect to the other of said jaws to define an openable and closable mouth between said tip portions of said jaws, said mouth being configured to be opened upon movement of said reciprocating linear member through said elongated tubular housing, whereupon said mouth is enabled to receive tissue therein, said reciprocating linear member being normally biased by a force to automatically close said mouth, said device being configured whereupon the closing of said mouth causes the movement of said reciprocating linear member along said central longitudinal axis a greater distance than the distance separating said tip portions of said jaws and said movement of said reciprocating linear member along said central longitudinal axis causes one of said marker and said indicator scale to move linearly along said central longitudinal axis with respect to the other of said marker and said indicator scale to provide a readily visible indication of the distance separating said tip portions of said jaws, and hence the thickness of tissue within said openable mouth.

2. The device of claim 1 wherein said reciprocating member comprises an elongated shaft.

3. The device of claim 2 wherein said force biasing said shaft is substantially constant to cause said tip portions of said jaws to apply a relatively constant force to the tissue within said mouth.

4. The device of claim 3 wherein said force biasing said shaft is provided by a spring.

5. The device of claim 4 wherein said spring is a preloaded compression spring.

6. The device of claim 5 additionally comprising a first bushing fixedly secured to said shaft and a second bushing fixedly secured to said tubular housing, and wherein said spring is interposed between said first and second bushing.

7. The device of claim 1 wherein said tubular housing includes a distal end and wherein said tip portions of said jaws extend out of said distal end of said tubular housing.

8. The device of claim 2 wherein said tubular housing includes a distal end and wherein said tip portions of said jaws extend out of said distal end of said tubular housing.

9. The device of claim 1 wherein both of said jaws are movable and wherein said jaws are pivotably connected to each other.

10. The device of claim 2 wherein both of said jaws are movable and wherein said jaws are pivotably connected to each other.

11. The device of claim 9 wherein each of said jaws comprises a first cam surface and wherein said tubular housing includes a distal end portion at which second cam surfaces are located, said second cam surfaces being configured to engage said first cam surfaces to pivot said jaws with respect to each other to open said mouth upon the movement of said elongated rod within said elongated tubular housing.

12. The device of claim 10 wherein each of said jaws comprises a first cam surface and wherein said tubular housing includes a distal end portion at which second cam surfaces are located, said second cam surfaces being configured to engage said first cam surfaces to pivot said jaws with respect to each other to open said mouth upon the movement of said elongated rod within said elongated tubular housing.

13. The device of claim 1 comprising an actuating mechanism for moving said reciprocating member, said actuating mechanism comprising a thumb button coupled to said reciprocating member and a finger grip member coupled to said tubular housing, said thumb button being configured to be manually moved with respect to said finger grip member to move said reciprocating member with respect to said tubular housing to effect the opening of said openable mouth.

14. The device of claim 2 comprising an actuating mechanism for moving said shaft, said actuating mechanism comprising a thumb button coupled to said shaft and a finger grip member coupled to said tubular housing, said thumb button being configured to be manually moved with respect to said finger grip member to move said shaft with respect to said tubular housing to effect the opening of said openable mouth.

15. The device of claim 2 wherein said marker is located on said elongated rod and wherein said elongated housing comprises a sleeve section through which said distal portion of said elongated rod extends, said sleeve section having a window and indicia extending along said window.

16. A method of measuring the thickness of tissue within the body of a patient comprising;
providing a laparoscopic device comprising an elongated tubular housing, a tissue thickness indicator, a reciprocating linear member and a pair of jaws, said elongated tubular housing having a central longitudinal axis and a proximal end portion, said tissue thickness indicator comprising a tubular section, an indicator scale and a marker, said tubular section being located at said proximal end portion of said elongated tubular housing and coaxial with said central longitudinal axis, said indicator scale comprising indicia disposed linearly along said central longitudinal axis, said reciprocating linear member being coupled to said tissue thickness indicator, said reciprocating linear member having a first portion configured for reciprocating linear movement in said tubular section, wherein one of said indicator scale and said marker is fixedly located at said proximal end portion of said elongated tubular housing and the other of said indicator scale and said marker is fixedly located at said proximal end portion of said reciprocating linear member, each of said jaws having a tip portion, at least one of said jaws being movable with respect to the other of said jaws to define an openable and closable mouth between said tip portions of said jaws;
inserting said laparoscopic device into the body of the patient to a situs of the tissue;
applying a force to a portion of said laparoscopic device against a bias on said reciprocating linear member to cause said reciprocating linear member to move through said tubular housing to open said mouth;
manipulating said laparoscopic device to locate said tissue in said open mouth;
releasing the force on said portion of said laparoscopic device, whereupon said mouth automatically closes, said reciprocating linear member being configured whereupon the closing of said mouth moves said reciprocating linear member a greater distance than the distance separating said tip portions of said jaws and said movement of said reciprocating linear member causes one of said marker and said indicator scale to move linearly with respect to the other of said marker and said indicator scale to provide a readily visible indication of the distance separating said tip portions of said jaws, and hence the thickness of tissue within said openable mouth.

17. The method of claim 16, wherein said method constitutes a portion of a bariatric procedure on the patient.

18. A laparoscopic device for measuring the thickness of tissue, said device having a central longitudinal axis and comprising:
a first elongated linear member extending linearly along said central longitudinal axis and having a proximal end portion;
a second elongated linear member extending linearly along said central longitudinal axis, one of said first and second elongated linear members being configured for reciprocation with respect to the other of said first and second linear elongated members;
a first jaw and a second jaw, at least one of said jaws being coupled to said other of said first and second elongated members, at least one of said first and second jaws being moveable along said central longitudinal axis, at least one of said first and second jaws being pivotable with respect to the other of said first and second jaws from a closed state to one of various open states, and vice versa, with the distance between said first and second jaws being different in each of said various open states;
a biasing member configured for biasing said jaws to said closed state; and
a tissue thickness indicator coupled to said jaws for indicating the distance between said jaws, wherein said tissue thickness indicator comprises a marker and a scale having plural indicia extending linearly along said central longitudinal axis, said marker being located at a fixed position on one of said first and second elongated members, said scale being located at a fixed position on the other of said first and second elongated members, one of said marker and said scale being movable linearly from a first position along said central longitudinal axis when said jaws are in said closed state to a second and different position along said central longitudinal axis when said jaws are in one of said open states, wherein the distance between said first position and said second position provides an indication of the distance between said jaws, and wherein the distance between said first and second positions is at least equal to the distance between said jaws.

19. The laparoscopic device of claim 18 wherein both of said first and second jaws are pivotable with respect to each other.

20. The laparoscopic device of claim 18 wherein said first elongated linear member is tubular, wherein said second elongated linear member is located within said first elongated linear member and configured to be reciprocated therein.

* * * * *